(12) United States Patent
Stepovich et al.

(10) Patent No.: US 8,162,917 B2
(45) Date of Patent: Apr. 24, 2012

(54) METHODS AND APPARATUS FOR BUFFERING ANESTHETICS

(75) Inventors: Matthew J. Stepovich, Santa Cruz, CA (US); Michael I. Falkel, Carmel Highlands, CA (US)

(73) Assignee: Onpharma, Inc., Los Gatos, CA (US)

( * ) Notice: Subject to any disclaimer, the term of this patent is extended or adjusted under 35 U.S.C. 154(b) by 450 days.

(21) Appl. No.: 12/406,670

(22) Filed: Mar. 18, 2009

(65) Prior Publication Data
US 2009/0292271 A1 Nov. 26, 2009

Related U.S. Application Data

(60) Provisional application No. 61/094,669, filed on Sep. 5, 2008, provisional application No. 61/054,930, filed on May 21, 2008.

(51) Int. Cl.
*A61B 19/00* (2006.01)
(52) U.S. Cl. ............ 604/415; 604/411; 604/416
(58) Field of Classification Search ............ 604/403, 604/411–416, 82, 84
See application file for complete search history.

(56) References Cited

U.S. PATENT DOCUMENTS

| | | |
|---|---|---|
| 1,616,202 A | 2/1927 | Shook et al. |
| 1,757,809 A | 5/1930 | Montuori |
| 2,484,657 A | 10/1949 | Son |
| 2,604,095 A | 7/1952 | Brody |
| 3,737,608 A | 6/1973 | Nagao et al. |
| 3,938,520 A * | 2/1976 | Scislowicz et al. ........ 604/405 |
| 3,993,751 A | 11/1976 | Zinke |
| 3,993,791 A | 11/1976 | Breed et al. |
| 4,154,820 A | 5/1979 | Simoons |
| 4,259,956 A | 4/1981 | Ogle |
| 4,513,015 A | 4/1985 | Clough |
| 4,630,727 A | 12/1986 | Feriani et al. |
| 4,654,204 A | 3/1987 | Copenhafer et al. |
| 4,704,088 A | 11/1987 | Newman |
| 4,753,345 A | 6/1988 | Goodsir et al. |
| 4,756,838 A | 7/1988 | Veltman |
| 4,795,441 A | 1/1989 | Bhatt |

(Continued)

FOREIGN PATENT DOCUMENTS

EP 0 298 067 A1 1/1989

OTHER PUBLICATIONS

International Search Report and Written Opinion of PCT Application No. PCT/US2009/043486, dated Jul. 2, 2009, 11 pages total.

(Continued)

*Primary Examiner* — Leslie Deak
(74) *Attorney, Agent, or Firm* — Wilson Sonsini Goodrich & Rosati

(57) ABSTRACT

A device for delivering buffer solution into a buffer cartridge comprises a needle assembly and a pusher. The septa of a buffer cartridge and an anesthetic cartridge are advanced onto a transfer needle, and the pusher advances a plunger into the buffer cartridge to deliver buffer through the transfer needle into the anesthetic cartridge. A separate exhaust needle allows excess anesthetic from the anesthetic cartridge to be exhausted. A compression member is usually provided to maintain a force against the plunger on the buffer cartridge to pressurize and stabilize the contents during sterilization and/or storage.

23 Claims, 4 Drawing Sheets

U.S. PATENT DOCUMENTS

| | | | |
|---|---|---|---|
| 4,959,175 | A | 9/1990 | Yatzidis |
| 5,049,129 | A * | 9/1991 | Zdeb et al. ............... 604/85 |
| 5,062,832 | A | 11/1991 | Seghi |
| 5,137,528 | A | 8/1992 | Crose |
| 5,149,320 | A | 9/1992 | Dhaliwal et al. |
| 5,211,643 | A | 5/1993 | Reinhardt et al. |
| 5,226,901 | A | 7/1993 | Dhaliwal et al. |
| 5,261,903 | A | 11/1993 | Dhaliwal et al. |
| 5,281,198 | A * | 1/1994 | Haber et al. ............... 604/86 |
| 5,296,242 | A | 3/1994 | Zander |
| 5,318,544 | A | 6/1994 | Drypen et al. |
| 5,330,426 | A | 7/1994 | Kriesel et al. |
| 5,383,324 | A | 1/1995 | Segers et al. |
| 5,439,643 | A | 8/1995 | Liebert |
| 5,542,934 | A | 8/1996 | Silver |
| 5,603,695 | A | 2/1997 | Erickson |
| 5,609,572 | A | 3/1997 | Lang |
| 5,609,838 | A | 3/1997 | Neuman et al. |
| 5,610,170 | A | 3/1997 | Inoue et al. |
| 5,690,215 | A | 11/1997 | Kimball et al. |
| 5,779,357 | A | 7/1998 | Jonsson et al. |
| 5,840,252 | A | 11/1998 | Giertych |
| 5,984,906 | A | 11/1999 | Bonnichsen et al. |
| 6,022,337 | A | 2/2000 | Herbst et al. |
| 6,232,128 | B1 | 5/2001 | Iguchi et al. |
| 6,432,089 | B1 | 8/2002 | Kakimi et al. |
| 6,620,138 | B1 | 9/2003 | Marrgi et al. |
| 6,692,468 | B1 | 2/2004 | Waldenburg |
| 6,818,179 | B1 | 11/2004 | Edgson et al. |
| 6,948,522 | B2 * | 9/2005 | Newbrough et al. ......... 137/550 |
| 7,445,801 | B2 | 11/2008 | Faict et al. |
| 7,462,164 | B2 | 12/2008 | Moir |
| 7,507,579 | B2 | 3/2009 | Boccazzi et al. |
| 2003/0015423 | A1 | 1/2003 | LaGreca et al. |
| 2004/0175437 | A1 | 9/2004 | Beckett |
| 2005/0113747 | A1 * | 5/2005 | Moir ............... 604/87 |
| 2007/0265593 | A1 | 11/2007 | Kitagawa et al. |
| 2007/0293441 | A1 | 12/2007 | Choo et al. |
| 2008/0045925 | A1 | 2/2008 | Stepovich et al. |
| 2009/0221984 | A1 | 9/2009 | Girgis et al. |
| 2011/0005958 | A1 | 1/2011 | Stepovich et al. |

OTHER PUBLICATIONS

Michaels, "Sterilisation of Sodium Bicarbonate Solutions," Pharm J. Sep. 4, 1984;107(4427):160-161.

U.S. Appl. No. 12/944,492, filed Nov. 11, 2010, Stepovich et al.

APP Pharmaceutical, LLC. Sodium bicarbonate 4.2% neutralizing additive solution (2.5mEq/ml). Product label, revised Apr. 2008.

Difazio, et al. Comparison of pH-adjusted lidocaine solutions for epidural anesthesia. Anesth Analg. Jul. 1986;65(7):760-4.

Fitton, et al. The use of pH adjusted lignocaine in controlling operative pain in the day surgery unit: a prospective, randomised trial. Br J Plast Surg. Sep. 1996;49(6):404-8.

Masters, et al. Randomised control trial of pH buffered lignocaine with adrenaline in outpatient operations. Br J Plast Surg. Jul. 1998;51(5):385-7.

McGlone, et al. Reducing the pain of intradermal lignocaine injection by pH buffering. Arch Emerg Med. Jun. 1990;7(2):65-8.

Metzinger, et al. Local anesthesia in blepharoplasty: a new look? South Med J. Feb. 1994;87(2):225-7.

Momsen, et al. [Neutralization of lidocaine-adrenaline. A simple method for less painful application of local anesthesia]. Ugeskr Laeger. Aug. 14, 2000;162(33):4391-4. (Article in Danish—English abstract only).

Nelson. Neutralizing pH of lidocaine reduces pain during Norplant system insertion procedure. Contraception. May 1995;51(5):299-301.

Palmon, et al. The effect of needle gauge and lidocaine pH on pain during intradermal injection. Anesth Analg. Feb. 1998;86(2):379-81.

Peterfreund, et al. pH adjustment of local anesthetic solutions with sodium bicarbonate: laboratory evaluation of alkalinization and precipitation. Reg Anesth. Nov.-Dec. 1989;14(6):265-70.

Ridenour, et al. Anesthetic efficacy of a combination of hyaluronidase and lidocaine with epinephrine in inferior alveolar nerve blocks. Anesth Prog. 2001 Winter;48(1):9-15.

Samdal, et al. Alkalisation of lignocaine-adrenaline reduces the amount of pain during subcutaneous injection of local anaesthetic. Scand J Plast Reconstr Surg Hand Surg. Mar. 1994;28(1):33-7.

Sapin, et al. Reduction in injection pain using buffered lidocaine as a local anesthetic before cardiac catheterization. Cathet Cardiovasc Diagn. Jun. 1991;23(2):100-2.

Schwab, et al. Bicarbonate buffering of local anesthetics. Am J Emerg Med. May 1996;14(3):339.

Whitcomb, et al. A prospective, randomized, double-blind study of the anesthetic efficacy of sodium bicarbonate buffered 2% lidocaine with 1:100,000 epinephrine in inferior alveolar nerve blocks. Anesth Prog. 2010 Summer;57(2):59-66.

* cited by examiner

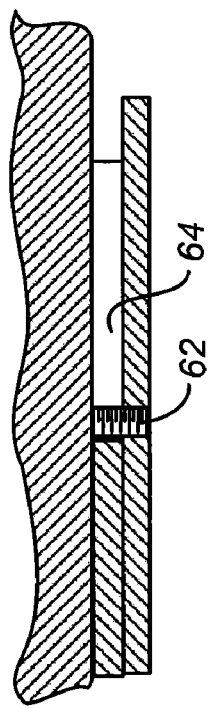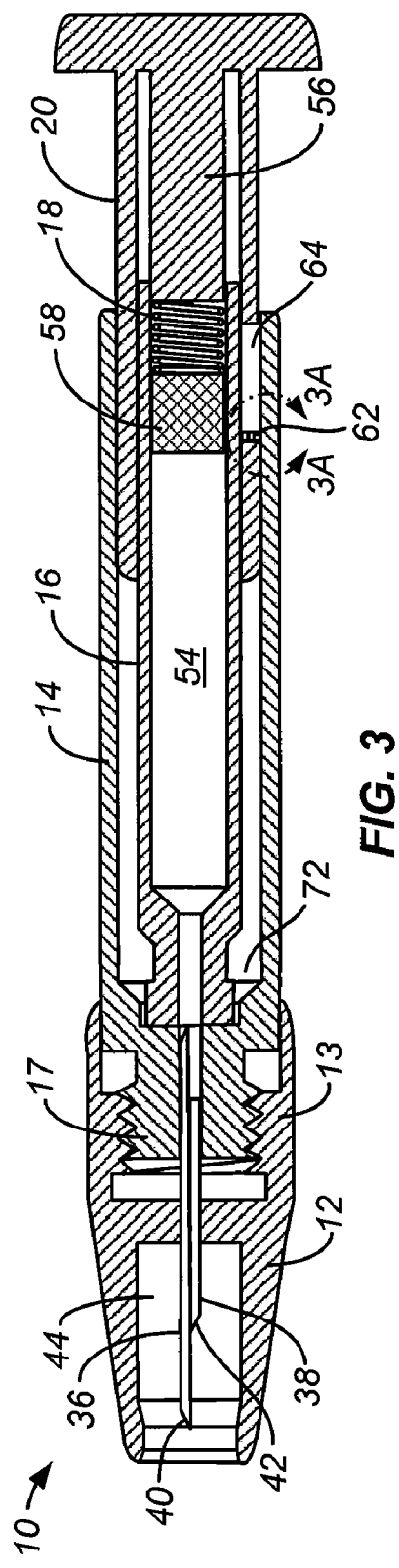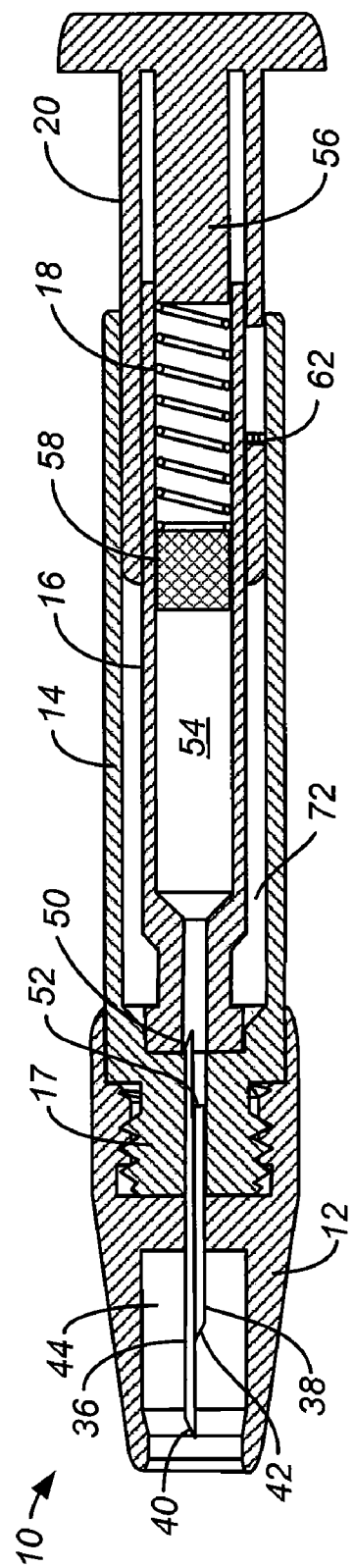

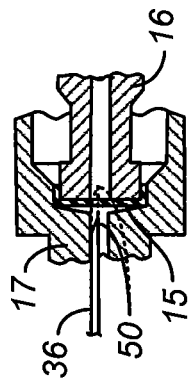
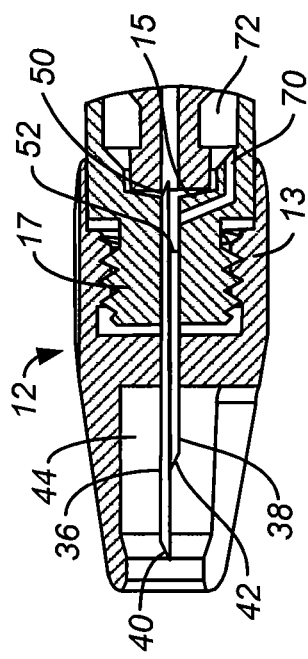
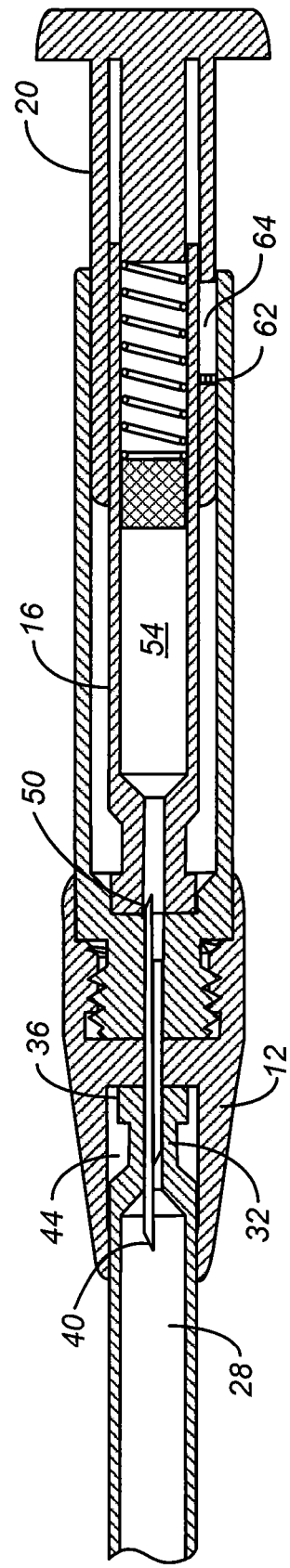
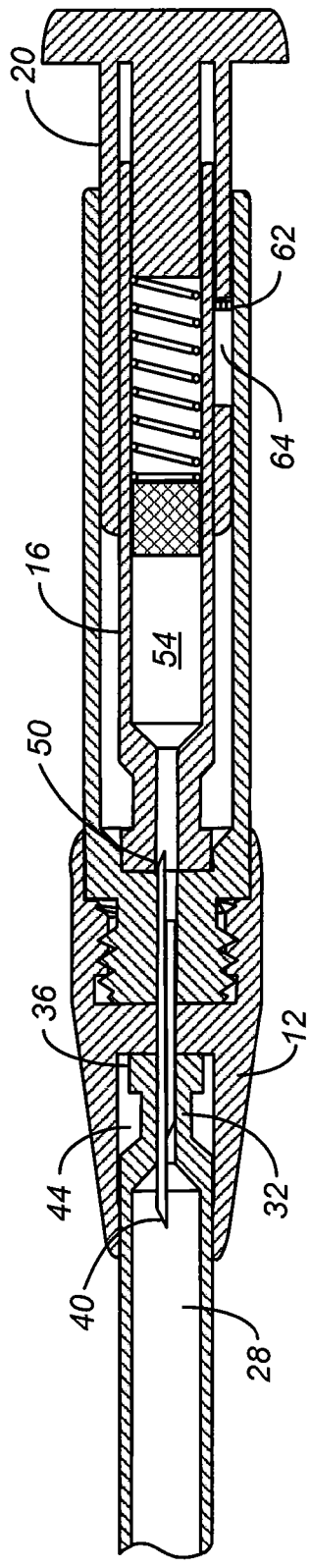
FIG. 5A
FIG. 5
FIG. 6
FIG. 7

METHODS AND APPARATUS FOR BUFFERING ANESTHETICS

CROSS-REFERENCES TO RELATED APPLICATIONS

This application claims the benefit of prior provisional application 61/054,930, filed on May 21, 2008, and of provisional application 61/094,669, filed on Sep. 5, 2008, the full disclosures of which are incorporated herein by reference.

BACKGROUND OF THE INVENTION

1. Field of the Invention

The present invention relates generally to methods and apparatus for buffering anesthetics. More particularly, the present invention relates to methods for preparing and storing sodium bicarbonate buffering solutions and combining such solutions with anesthetics stored in small cartridges.

Aqueous solutions containing bicarbonate ions are used in various medical applications such as antidotes, dialysates, artificial cerebrospinal fluid, intraocular irrigating solutions, cardiac perfusates, cardioplegic solutions, peritoneal irrigating solutions, and solutions for organ preservation, etc. Of particular interest to the present application bicarbonates solutions are used to buffer dental and other anesthetics to control pH. One of the most commonly used medical bicarbonate solutions consists of sodium bicarbonate ($NaHCO_3$) mixed with water ($H_2O$). In medical bicarbonate solutions, bicarbonate ions are in equilibrium as represented by the following expression:

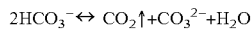

$$2HCO_3^- \leftrightarrow CO_2\uparrow + CO_3^{2-} + H_2O$$

If the reaction occurs in a closed system, equilibrium is reached with the amounts of reactants remaining constant. In open systems, however, the carbon dioxide gas escapes and the reaction proceeds from the left to the right with bicarbonate ($2HCO_3$) evolving into carbon dioxide gas ($CO_2$), carbonate ($CO_3$) and water ($H_2O$), progressively decreasing the concentration of bicarbonate ions and increasing the concentration of carbonate ions. Since carbonate ions are more alkaline than bicarbonate ions, the pH of the solution will progressively increase.

Clinical effectiveness of bicarbonate medical solutions often depends on maintenance of a particular pH range, generally from 7 to 9. For some applications, maintaining the pH in a more narrow range is beneficial. To stabilize pH and CO2 content, sodium bicarbonate solutions are conventionally packed in gas tight containers that limit leakage of evolved carbon dioxide into the atmosphere. By limiting the loss of evolved CO2 pH change may be reduced. As CO2 leaves solution and enters the container's "headspace" (the gas-filled region above the solution) the partial pressure of the evolved CO2 will increase and eventually establish equilibrium between CO2 leaving solution and CO2 returning to solution.

The gas tight container most commonly used to store medical bicarbonate solutions is the glass vial with a pierceable rubber cap, the cap being referred to as a septum. Such vials allow the medical practitioner to pierce the septum with a hypodermic needle and withdraw or "draw up" a desired volume of bicarbonate solution into a syringe. To facilitate withdrawing the bicarbonate, the vials typically include a significant headspace that prevents a vacuum from forming when the practitioner attempts to draw up the fluid. Once the fluid is drawn up into a syringe, the syringe can be used to deliver the fluid into a catheter or a blood vessel. Of particular interest to the present invention, the partially filled syringe may be used to draw up a second solution, such as a local anesthetic, from another vial in order to mix the second solution with the sodium bicarbonate, where the syringe serves as a mixing and delivery vessel for the resulting pH buffered solution.

One drawback to using such vial-and-syringe systems for storing, mixing, and/or delivering bicarbonate solutions is that drawing up the solution into the syringe reduces pressure over the bicarbonate solution which allows $CO_2$ to leave solution and create $CO_2$ bubbles in the solution during the transfer. Also, there can be significant agitation of the solution as the bubbles enter the syringe, further causing $CO_2$ to dissolve out of solution. For these reasons, even if the pH of a sodium bicarbonate buffering solution in a vial-type storage container were estimated or ascertained before delivery, drawing up, mixing and/or delivery of the bicarbonate system may alter the pH of the solution to an undesirable extent.

One particular device for combining a buffer solution, such as sodium bicarbonate, with an anesthetic, such as a dental anesthetic in a conventional cartridge, is described in U.S. Pat. No. 5,603,695. The device comprises a buffer cartridge having a needle which may be penetrated through the septum of the anesthetic cartridge. The buffer is stored in a cartridge with significant head space and no provision for maintaining volatile $CO_2$ in solution in a bicarbonate anesthetic. Moreover, no provision is made for displacing anesthetic from the anesthetic cartridge as the buffer is introduced.

For these reasons, it would be desirable to provide improved methods and apparatus for combining buffer solutions with anesthetics or other medical solutions, particularly where the buffer solutions are held in conventional glass cartridges. It would be particularly beneficial if the methods and devices employed buffer cartridges which maintained the buffer solution, more particularly sodium bicarbonate solution, in a stable condition with minimal pH change and carbon dioxide loss prior to use. It would be still further desirable if the methods and systems provided for introducing and combining the buffer solutions with anesthetic solution, where the anesthetic solution is held in conventional cartridges, without delivering an excess volume of buffer to the anesthetic cartridge, and relieving or exhausting an equal volume of anesthetic from the cartridge. At least some of these objectives will be met by the inventions described hereinbelow.

2. Description of the Background Art

Glass vials and cartridges for storing medical solutions are described in U.S. Pat. Nos. 1,757,809; 2,484,657; 4,259,956; 5,062,832; 5,137,528; 5,149,320; 5,226,901; 5,330,426; and 6,022,337. Injection pens which employ drug cartridges are described in U.S. Pat. No. 5,984,906. A particular disposable drug cartridge that can find use in the present invention is described in U.S. Pat. No. 5,603,695. A device for delivering a buffering agent into an anesthetic cartridge using a transfer needle is described in U.S. Pat. No. 5,603,695. Devices for maintaining a dissolved gas in solution in a pouch are described in U.S. Pat. Nos. 5,690,215; 5,610,170; and 4,513,015, and U.S. Patent Publ. No. 2007/0265593. Other patents and applications of interest include U.S. Pat. Nos. 2,604,095; 3,993,791; 4,154,820; 4,630,727; 4,654,204; 4,756,838; 4,959,175; 5,296,242; 5,383,324; 5,603,695; 5,609,838; 5,779,357; and U.S. Patent Publ. No. 2004/0175437.

BRIEF SUMMARY OF THE INVENTION

The present invention provides methods and apparatus for buffering anesthetics or other medical solutions held in a conventional cartridge, particularly those having a penetrable septum and a slidable plunger or plug, such as those generally described in U.S. Pat. No. 5,603,695 the full disclosure of which is incorporated herein by reference. Such cartridges are commonly used in dental practice, particularly for delivering anesthetics to a patient prior to a procedure. Such cartridges are conventionally loaded into a syringe or other delivery device, where the syringe engages the plunger in the cartridge to dispense the anesthetic through a needle which has penetrated through the septum. To optimize effectiveness of the anesthetics and to reduce injection pain, it is desirable to buffer conventional anesthetics, typically dental anesthetics such as lidocaine, articaine, prilocaine, or mepivacaine, shortly before use. It is very important, however, that the buffering solutions themselves have predictable, stable pHs and chemical compositions in order for the buffered anesthetic to achieve an optimum effect and minimum injection pain.

Methods according to the present invention for buffering such anesthetic cartridges comprise providing a buffer cartridge, where the buffer cartridge typically also has a septum and plunger and which may often be similar or identical to the construction of the anesthetic cartridge. A transfer needle is penetrated through septums on both the buffer cartridge the anesthetic cartridge to provide a fluid transfer path therebetween. An exhaust needle is also penetrated through the septum on the buffer cartridge but not through the septum on the anesthetic cartridge. By advancing the plunger on the buffer cartridge, a volume of buffer may be transferred from the buffer cartridge into the anesthetic cartridge while an equal volume of anesthetic is expelled from the anesthetic cartridge through the exhaust needle, usually into a waste receptacle as described hereinbelow. Simultaneously expelling the anesthetic allows a predetermined volume of buffer to be introduced into the anesthetic cartridge without overfilling the anesthetic cartridge or causing the plunger in the anesthetic cartridge to be pushed out by the excess volume.

In a preferred aspect of the present invention, the stability of the buffer solution may be maintained prior to its use at or near a specified pH by filling the cartridge with buffering solution of the desired pH and then applying sufficient pressure to the buffer solution to inhibit vaporization of a volatile species, such as vaporization and loss of carbon dioxide from bicarbonate buffers where the level of pressure depends on the pH as well as the maximum temperature to be encountered in shipping and storage. Where, for example, the buffer comprises 8.4% sodium bicarbonate, the pH is to be maintained at 7.62, and the maximum expected temperature is 25° C., a force must be applied which is sufficient to maintain an absolute pressure within the buffer cartridge at least as high as the equilibrium partial pressure of carbon dioxide gas in an 8.4% sodium bicarbonate solution at pH 7.62 at a temperature of 25° C. maximum, which according to the Henderson-Hasselbach equation and Henry's Law, is 1.64 atmospheres. A greater force will usually be applied to create a margin of safety in case of higher than expected storage or transport temperatures. Where the cartridge is expected to undergo heat sterilization, the force applied should be sufficient to create a pressure of at least 6 atmospheres, typically higher for a margin of safety.

In exemplary embodiments, the force is applied by engaging a spring held under compression against the plunger or by using a plunger which is formed from a compressible resilient material or otherwise made compressible so that when compressed a specified distance by a pusher, the solution in the cartridge will be placed under a pre-determined amount of pressure. By way of example, if the target pH is 7.62, the needed pressure is at least 1.64 atmospheres (as described above), and the plunger has an area exposed to the anesthetic of approximately 37 mm$^2$, a spring would need to apply a minimum force against the plunger of 9.4 lbs/in$^2$. The force will depend both on the spring constant and the depth of spring compression.

While the application of a constant positive pressure against the buffer held in a buffer cartridge would generally be sufficient to maintain stability, it will be preferred to completely remove the air and other gases from the buffer cartridge prior to sealing. By removing all "head space," the volatile species, such as carbon dioxide in bicarbonate buffers, will be held in solution by the elevated pressure with little or no loss. The presence of even a small gas head space will allow the loss of some carbon dioxide or other volatile species resulting in a small but measurable change in the pH and composition of the buffer as the volatile species reaches an equilibrium partial pressure. Moreover, the lack of a headspace prevents gases in the headspace from being driven into solution by the positive pressure, which might alter the chemical properties of the buffer.

In specific aspects of the method of the present invention, penetrating the transfer needle may comprise turning a knob which holds the transfer and exhaust needles to advance the transfer needle through the buffer cartridge septum. Thus, penetrating the transfer needle and the exhaust needle through the anesthetic cartridge septum usually occurs as the anesthetic cartridge is inserted into a receptacle on the knob. Preferably, the exhaust needle directs the expelled anesthetic into a reservoir. For instance in an exemplary embodiment, the expelled anesthetic could flow into a space in a housing that surrounds the buffer cartridge. The space may include an absorbent material. Advancing the plunger on the buffer cartridge usually comprises engaging a pusher against the plunger and advancing the pusher to cause the plunger to proceed along the interior of the cartridge, driving the plunger against the buffer therein, and forcing the buffer into the transfer needle. Typically, the pusher will be reciprocatably mounted on the housing in which the buffer cartridge is held.

In a further specific aspect of the method of the present invention, the volume of buffer dispensed may be controlled by advancing the pusher until it engages a first stop, usually on the housing, which defines a first delivered volume of buffer. Second and subsequent delivered volumes may be dispensed by advancing the pusher beyond the first stop until the pusher engages a second stop to define a second delivered volume, and optionally further stops to define further delivered volumes. Such multiple delivered volumes of buffer may be used with a single anesthetic cartridge or with successive anesthetic cartridges which are connected to the buffer delivery apparatus sequentially.

Devices according to the present invention are intended for transferring a volume of buffer solution from a buffer cartridge into an anesthetic cartridge. The buffer cartridge typically comprises a hollow tube sealed on one end and having a slidable plug on the other with the buffering solution being held in a space therebetween. The devices also comprise a needle assembly having a transfer needle and an exhaust needle, where the transfer needle can be advanced to penetrate the septum on the buffer cartridge. The needle assembly also detachably receives an anesthetic cartridge so that the transfer and exhaust needles penetrate a septum thereon. The devices also comprise a pusher that advances the plunger on the buffer cartridge to transfer buffer through the transfer needle into the anesthetic cartridge while excess anesthetic is exhausted from the anesthetic cartridge as the anesthetic is displaced by buffer. In alternative embodiments, a slightly modified buffer cartridge is used. In such embodiments the cartridge is a hollow tube open on only one end and the slidable plunger acts as both plunger and septum, meaning that the transfer needle pierces the plunger itself to create a fluid path for the buffer solution to flow out of the buffer cartridge and into the anesthetic cartridge. As the pusher advances the plunger down the glass tube, the solution is forced out the transfer needle into the anesthetic cartridge.

The devices of the present invention will typically further include a housing having an attachment end, an open end, and an open interior. The interior of the housing receives the buffer cartridge with the septum of the buffer cartridge adjacent the attachment end and the plunger of the buffer cartridge adjacent the open end. The devices usually further include a knob which threadably connects to the attachment end of the housing, where the needle assembly is carried by the knob so that turning the knob advances the transfer needle into the buffer cartridge. The transfer and exhaust needles will extend into an anesthetic cartridge receptacle on the knob so that insertion of the anesthetic cartridge into the receptacle causes the transfer and exhaust needles to penetrate through a septum on the anesthetic cartridge.

In order to pressurize and stabilize the buffer within the buffer cartridge, the devices will typically further comprise a compression member which is disposed between the pusher and the plunger of the buffer cartridge. The compression member is compressed or otherwise adapted to apply a predetermined force on the plunger when the pusher is advanced or positioned at a predetermined distance relative to the buffer cartridge. Usually, the compression member will be a coil spring, and the device will further comprise a lock which holds the pusher at the predetermined advance distance relative to the buffer cartridge. Advantageously, once the transfer needle penetrates the septum on the buffer cartridge, the pressure will be released and the spring or other compression member will advance and cause a small volume of the buffer to pass through and prime the transfer needle, removing residual gases.

At least one stop will be provided on the device, typically on the housing, to control a first advancement stroke of the pusher to deliver a first predetermined volume of the buffer into the anesthetic cartridge. Optionally, a second stop may be provided, again typically on the housing, to control or limit advancement of the pusher beyond the pusher beyond the first stop to deliver a second predetermined volume of buffer as the pusher is further advanced. Additional stops can be incorporated to allow for more than two predetermined volumes. Other embodiments incorporate mechanisms that allow the practitioner to adjust the volume to be delivered.

In a further aspect of the present invention, a method for storing the bicarbonate buffer solution comprises providing a cartridge having an open interior, a needle penetrable septum, and a plunger which can be advanced into the open interior to pressurize the contents thereof. The cartridge is filled with a solution of bicarbonate buffer that will evolve carbon dioxide at room temperature and pressure. Evolution of the carbon dioxide is inhibited by storing the cartridge while applying a force to the plunger, where the force is sufficient to pressurize the bicarbonate buffer solution at a pressure which inhibits the evolution of carbon dioxide, thus stabilizing the pH and composition of the buffer. In exemplary embodiments, the buffer comprises sodium bicarbonate having a pH in the range from 7.5 to 7.8 and the applied pressure is above 1.2 atmospheres with preferred pH and pressure ranges set forth above. In further exemplary embodiments, the force is applied by compressing a spring or other compression member against the plunger and maintaining the pressure until the cartridge is used. Preferably, the cartridge is filled with all gases evacuated (the headspace eliminated) to further stabilize the pH and carbonate content of the solution.

In a still further aspect of the present invention, a bicarbonate buffer storage assembly comprises a buffer cartridge, as described above, and a mechanism for placing the buffer solution therein under pressure. In one embodiment, the storage assembly houses the buffer cartridge and includes a compression member that exerts a force on the plunger, the force pressurizing the bicarbonate buffer solution sufficiently to inhibit evolution of carbon dioxide expected storage temperatures, usually above 1.2 atm. In still other embodiments, the pressure would be sufficient to inhibit evolution of carbon dioxide at autoclave temperatures, usually above 5 atm.

In preferred embodiments, the open interior of the cartridge is completely filled with sodium bicarbonate with significantly no head space remaining. The compression member may comprise a compressible spring which is maintained in compression and engages the plunger. Usually, the compressible spring is a coil spring, and the cartridge assembly further comprises a housing where the cartridge is disposed within the housing and the coil spring is held in compression between the housing and the plunger.

BRIEF DESCRIPTION OF THE DRAWINGS

FIG. 3 is a cross-sectional view of the buffer transfer device of FIGS. 1 and 2 shown prior to penetrating a transfer needle through a septum of the buffer cartridge where the spring remains under compression applying pressure to the buffer within the buffer cartridge.

FIG. 3A is a detailed view of a stop member taken along line 3A-3A of FIG. 3.

FIG. 4 is a cross-sectional view of the buffer transfer device similar to FIG. 3, except that the transfer needle has been penetrated through the septum of the buffer cartridge and the release of pressure has allowed the spring to advance a plunger of the buffer cartridge to expel a small volume of the buffer and prime the transfer needle.

FIG. 5 is an enlarged, detailed cross-sectional view of the knob and needle components of the buffer transfer device of the present invention.

FIG. 5A is a further enlarged, detailed cross-sectional view illustrating the septum on the buffer cartridge.

FIG. 6 is a cross-sectional view of a buffer transfer device similar to that shown in FIGS. 3 and 4 except that an anesthetic cartridge has been inserted into a receptacle formed in the knob to cause the transfer needle and an exhaust needle to penetrate a septum of the anesthetic cartridge.

FIG. 7 is a cross-sectional view similar to those of FIGS. 3, 4, and 6, except that the pusher has been advanced through a first length of travel in order to deliver a first volume of buffer from the buffer cartridge into the attached anesthetic cartridge.

DETAILED DESCRIPTION OF THE INVENTION

Figure 1:
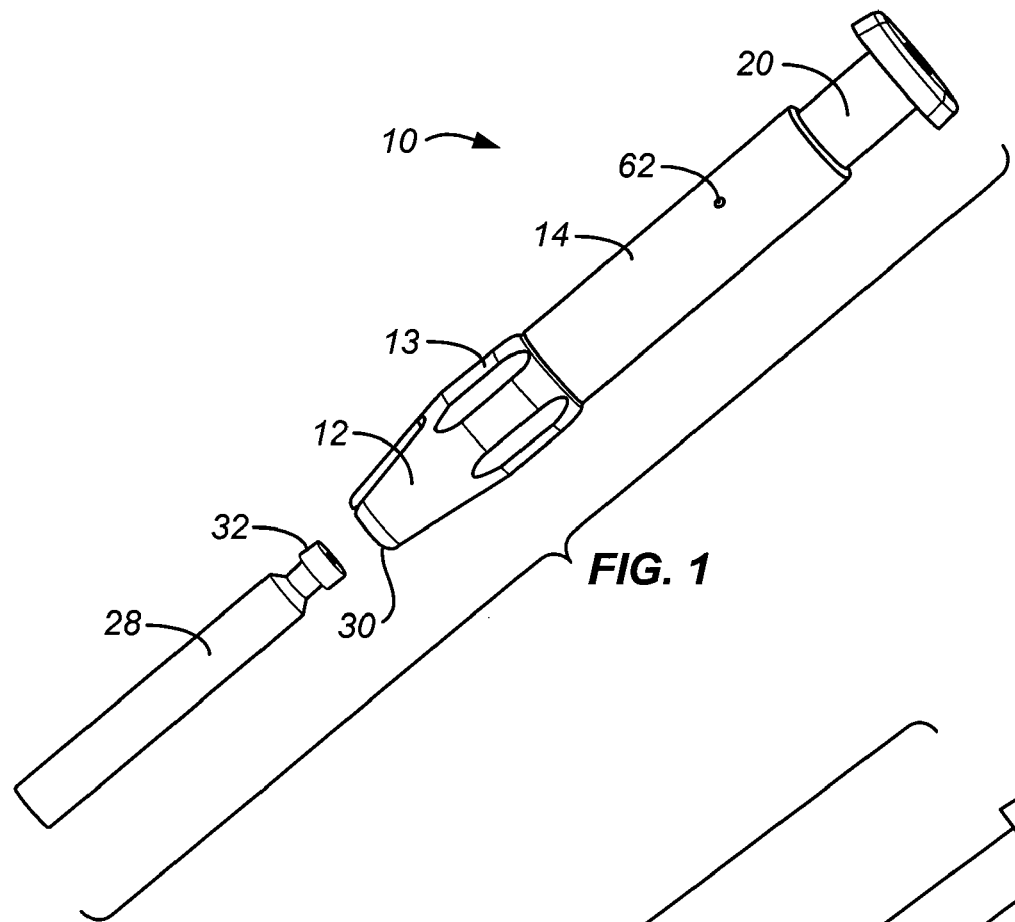
FIG. 1 is a perspective view illustrating the buffer transfer device of the present invention and a conventional anesthetic cartridge.
Figure 2:
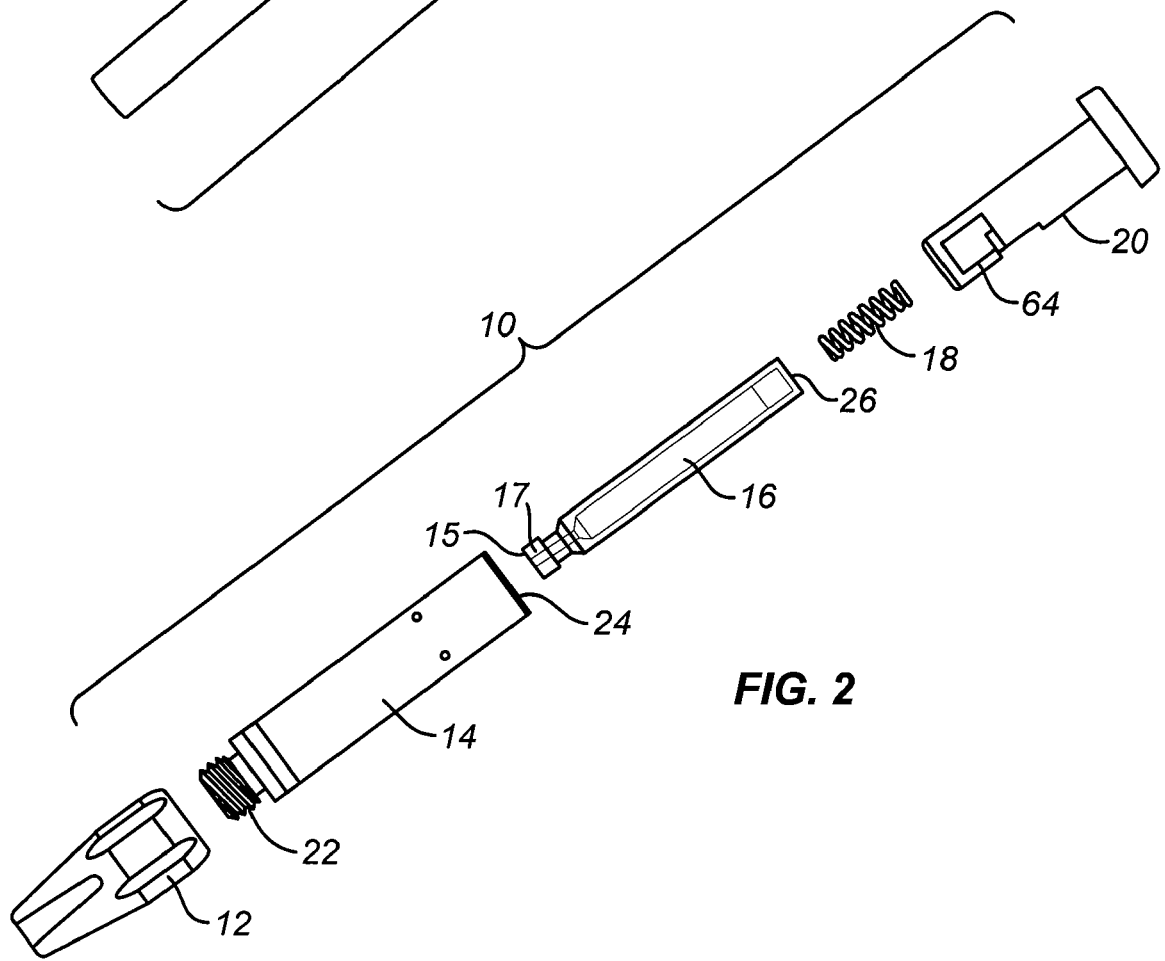
FIG. 2 is an exploded view of the buffer transfer device illustrating the knob, housing, buffer cartridge, spring, and pusher components thereof.

Referring to FIGS. 1 and 2, a buffer transfer device 10 comprises a knob 12, and housing 14, a buffer cartridge 16, a spring 18 or other compression member, and a pusher 20. The knob 12 is rotatably mounted on threads 22 at the distal end of the housing 14 and the buffer cartridge 16 may be inserted into an open proximal end 24 of the housing. The pusher 20 is introduced through the open end 24 and compresses the spring 18 engaged against a proximal end 26 of the buffer cartridge 16, as will be described in greater detail below. The buffer transfer device 10 detachably receives a conventional anesthetic cartridge 28 within a receptacle 44 (best seen in FIG. 5) at the distal end 30 of the knob 12, which also will be described in greater detail below.

Typically, buffer transfer device 10 will be fully assembled at a central, sterile location and distributed for use. While the temperature and other conditions of distribution can be somewhat controlled, it will be appreciated that a variety of temperatures and other potentially destabilizing conditions might be encountered during distribution and storage prior to use of the device for buffering the anesthetic cartridge. A mechanism for maintaining pressure on the buffer solution within the buffer cartridge 16 will be provided in order to limit the loss of carbon dioxide or other volatile components from bicarbonate or other buffering solutions. The details of the pressurization mechanism are described below.

Referring now to FIG. 3, the buffer transfer device 10 in its pre-use or storage configuration is illustrated. The knob 12 includes a transfer needle 36 and an exhaust needle 38, both of which can be more clearly seen in the detailed view of FIG. 5. The transfer and exhaust needles 36 and 38 are illustrated as separate hypotubes or other tubular structures. It will be appreciated, however, they could also be formed as a single, bitumen structure, although in all cases, a distal tip 40 of the transfer needle should extend distally beyond a distal tip 42 of the exhaust needle 38. The distal portions of both needles 36 and 38 extend into a receptacle region 44 which receives the septum end 32 of the anesthetic cartridge 28, as will be described in more detail below with respect to FIGS. 5 and 6. By axially spacing apart the distal tips 40 an 42 of the transfer and exhaust needles 36 and 38, mixing between the buffer which is being introduced through the transfer needle and the anesthetic which is being expelled through the exhaust needle will be minimized.

The transfer needle 36 has a proximal end 50 which extends into a threaded region 13 of the knob 12, as best seen in FIG. 5. Proximal end 50 extends sufficiently far so that it will penetrate a septum 15 (best seen in FIG. 5A) formed over the neck 17 of the buffer cartridge 16 when the knob 12 is fully tightened on the threads 17 of the housing 14, as shown in FIG. 4. In contrast, proximal end 52 of the exhaust needle 38 terminates distally of the septum 15 even when the knob is fully tightened.

The knob 12 will be tightened over the housing 14 before the anesthetic cartridge 28 is introduced to the receptacle 44. Prior to tightening the knob, the septum 15 remains intact and pressure of buffer within the interior 54 of the cartridge 16 remains above atmospheric as provided by the pressure of spring 18. Spring 18, in turn, remains compressed between extension member 56 of the pusher 20 and a plunger 58 which is slidably received within the open proximal end of the buffer cartridge 16. As soon as the proximal end 50 of transfer needle 36 penetrates the septum 15, as shown in FIG. 4, the pressure on the buffer in interior 54 is released, causing a small flow of buffer through the transfer needle and out through the distal tip 40 in order to prime the transfer needle. The plunger 58 advances under the force of spring 18, and the buffer transfer device 10 is in the condition illustrated in FIG. 4. Note that the proximal movement of the pusher 20 is prevented by a stop member 62 fixed in a wall of the housing 14, as illustrated in FIG. 3A. Stop member 62 engages an edge of window 64 formed in the wall of the pusher 20, as will be described in greater detail below in connection with FIGS. 8A-8D. Preventing the pusher 20 from moving proximally is necessary to maintain the pressure applied by spring 18 on the anesthetic within the interior 54 of the anesthetic cartridge 16.

Referring now to FIG. 6, after the knob 12 has been tightened and the proximal tip 50 of transfer needle 36 has penetrated the septum 15 of buffer cartridge 16, the neck 32 of anesthetic cartridge 28 may be inserted into the receptacle 44 of knob 12, as illustrated in FIG. 6. A first volume of the buffer may then be advanced from the interior 54 of buffer cartridge 16 through transfer needle 36 by distally advancing the pusher 20, as shown in FIG. 7. The length of travel of pusher 20, and thus volume of buffer delivered into the anesthetic cartridge 28, is controlled by travel of the stop member 62 in the window 64. Prior to transferring any buffer, the stop member 62 is positioned at a left hand edge of the window 64, as seen in FIG. 6. The pusher 20 may then be advanced until the stop member 62 engages a right hand edge of the window 64, as shown in FIG. 7.

As the plunger is advanced, transferring buffer through transfer 36 into the anesthetic cartridge 28, an equal volume of anesthetic will flow through the distal end 42 of the exhaust needle 38 and out the proximal end 52 thereof into the neck region 17 of the housing 14. While the exhausted anesthetic is wasted, it is desirable that it be contained within the buffer transfer device to avoid spilling and contamination. To that end, an exhaust passage 70 (FIG. 5) may be formed in the neck 17 to allow the excess anesthetic to flow into a waste receptacle 72 which is formed in the interior of the housing 14 surrounding the exterior of the buffer cartridge 16.

Figure 8A:
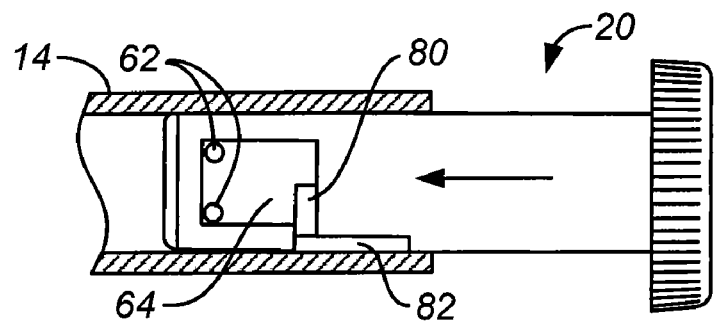
FIGS. 8A-8D are schematic illustrations of stop members on the housing which limit and control travel of the pusher to allow first and second sequential volume deliveries from the buffer transfer device.
Figure 8B:
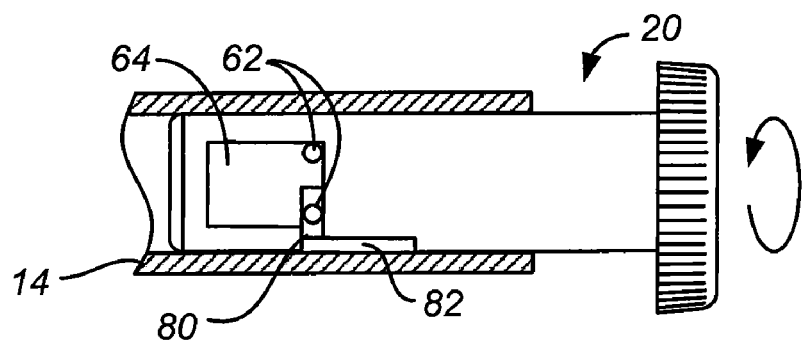
Figure 8C:
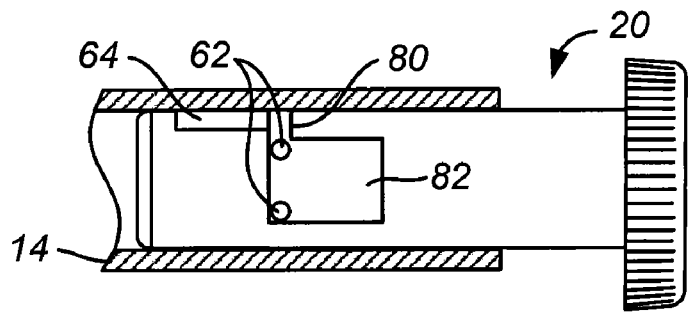
Figure 8D:
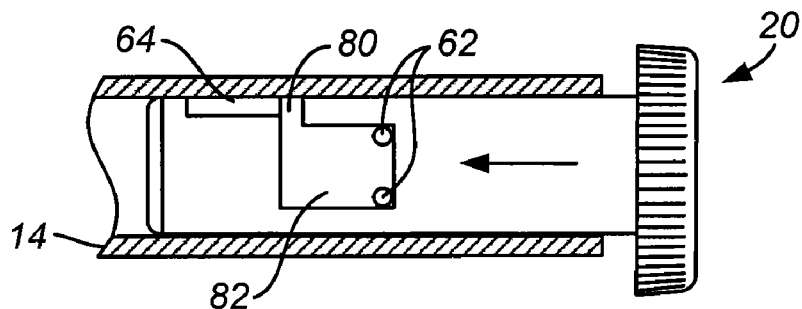

Referring now to FIGS. 8A-8D, advancement of the pusher 20 relative to the housing 14 as controlled by the stop members 62 will be described in more detail. In FIG. 8A, the pusher is shown in the configuration of FIGS. 3, 4, and 6 before the plunger has been advanced or otherwise moved. The stop members 62 (only one of which is visible in FIGS. 3, 4, and 6) are engaged against the left hand wall (as shown in FIGS. 8A-8D) of window 64. When the pusher 20 is advanced to transfer buffer into the anesthetic cartridge, as shown in FIG. 8B, the stop members 62 translate to engage the right hand edge of window 64, stopping advancement of the pusher. If only a single delivery is required, no further structure or manipulations would be needed. However, by providing a second window 82 and the ability to rotate the pusher 20 about its axis, a second delivery volume may be provided. A passage 80 is provided between windows 64 and 62 to allow rotation of the pusher 20 so that the stop members 62 move from window 64 into the second window 82. As the second window 82 is offset to the right relative to the first window 64, further leftward travel out of the pusher is now allowed, until the stop members 62 engage the right hand edge of window 82, as shown in FIG. 8B. A second measured volume of the buffer may be delivered. It will be appreciated that still further window mechanisms could be provided for allowing third, fourth, and perhaps even more volumes of buffer to be delivered from a single buffer transfer device.

While the above is a complete description of the preferred embodiments of the invention, various alternatives, modifications, additions, and substitutions are possible without departing from the scope thereof, which is defined by the claims.

What is claimed is:

1. A method for buffering an anesthetic cartridge, said method comprising:
   providing an anesthetic cartridge having a septum;

providing a buffer cartridge having a septum and plunger;
penetrating a transfer needle through the septum on the buffer cartridge and the septum on the anesthetic cartridge, whereby a fluid transfer path is established;
penetrating an exhaust needle through the septum on the anesthetic cartridge but not the septum on the buffer cartridge; and
advancing the plunger on the buffer cartridge to transfer a volume of buffer from the buffer cartridge into the anesthetic cartridge while causing an equal volume of anesthetic to be expelled from the anesthetic cartridge through the exhaust needle.

2. A method as in claim 1, wherein, prior to penetrating the transfer needle and advancing the plunger, a force is applied to the buffer in the buffer cartridge to inhibit the vaporization of volatile species.

3. A method as in claim 2, wherein the buffer comprises sodium bicarbonate having a pH in the range from 7.5 to 7.8 and a force is applied which is sufficient to maintain a pressure above 1.2 atm within the cartridge to prevent the vaporization of $CO_2$ at normal storage temperatures.

4. A method as in claim 2, wherein the buffer comprises sodium bicarbonate and a force is applied which is sufficient to maintain a pressure above 5 atm within the cartridge to prevent the vaporization of $CO_2$ at heat sterilization temperatures.

5. A method as in claim 2, wherein the force is applied by a spring held under compression against the plunger.

6. A method as in claim 1, wherein the penetrating comprises turning a knob which holds the transfer and exhaust needles to advance the transfer needle through the buffer cartridge septum.

7. A method as in claim 6, wherein penetrating the transfer of exhaust needles through the anesthetic cartridge septum occurs as the anesthetic cartridge is inserted into a receptacle on the knob.

8. A method as in claim 1, wherein the exhaust needle directs the expelled anesthetic into a reservoir.

9. A method as in claim 8, wherein the reservoir is disposed in a hanging surrounding the buffer cartridge.

10. A method as in claim 1, wherein advancing the plunger on the buffer cartridge comprises engaging a pusher against the plunger and advancing the pusher.

11. A method as in claim 10, wherein the pusher is advanced until it engages a first stop to define a first delivered volume of buffer.

12. A method as in claim 11, further comprising advancing the pusher beyond the first stop until the pusher engages a second stop to define a second delivered volume.

13. A method as in claim 12, further comprising replacing the anesthetic cartridge after transferring the first delivered volume and before transferring the second delivered volume.

14. A device for transferring a volume of buffer solution into an anesthetic cartridge, said device comprising:
a buffer cartridge having a septum and a plunger;
a needle assembly having a transfer needle and an exhaust needle, and
a pusher which engages the plunger on the buffer cartridge;
wherein the transfer needle penetrates the septum of the buffer cartridge, the needle assembly detachably receives an anesthetic cartridge, and the transfer and exhaust needles penetrate a septum on the anesthetic cartridge so that the pusher can advance the plunger on the buffer cartridge to transfer buffer through the transfer needle into the anesthetic cartridge and excess anesthetic from the anesthetic cartridge is exhausted through the exhaust needle;
further comprising a first stop which limits advancement of the pusher to deliver a first volume of buffer as the pusher is advanced.

15. A device as in claim 14, further comprising a housing having an end adapted to detachably receive the anesthetic cartridge, and an interior having an open end for receiving the buffer cartridge with the septum adjacent to the end adapted to detachably receive the anesthetic cartridge and the plunger adjacent the open end.

16. A device as in claim 15, further comprising a knob which threadably connects to the attachment end of the housing, wherein the needle assembly is carried by the knob so that turning the knob advances the transfer needle into the buffer cartridge.

17. A device as in claim 16, wherein the transfer and exhaust needles extend into an anesthetic cartridge receptacle on the knob so that inserting the anesthetic cartridge into the receptacle penetrates the transfer and exhaust needles through a septum of the anesthetic cartridge.

18. A device as in claim 14, further comprising a compression member disposed to apply a predetermined force on the plunger when the pusher is advanced by a predetermined distance relative to the buffer cartridge prior to the transfer needle penetrating the septum on the buffer cartridge.

19. A device as in claim 18, wherein the compression member is a coil spring positioned between the pusher and the plunger on the buffer cartridge.

20. A device as in claim 18, wherein the pusher comprises the compression member.

21. A device as in claim 18, further comprising a lock which holds the pusher at said predetermined advanced distance relative to the buffer cartridge.

22. A device as in claim 14, further comprising a second stop which limits advancement of the pusher beyond the first stop to deliver a second volume of buffer as the pusher is advanced.

23. A device as in claim 14, further comprising a receptacle for receiving and holding the excess anesthetic which is exhausted through the exhaust needle.

* * * * *